United States Patent [19]
Delansorne et al.

[11] Patent Number: 6,153,587
[45] Date of Patent: Nov. 28, 2000

[54] CONFORMATIONALLY CONSTRAINED LH-RH ANALOGUES, THEIR USES AND PHARMACEUTICAL COMPOSITIONS CONTAINING THEM

[75] Inventors: Remi Delansorne; Jacques Paris, both of Nice, France

[73] Assignee: Laboratoire THERAMEX, Monaco

[21] Appl. No.: 09/317,125

[22] Filed: May 24, 1999

Related U.S. Application Data

[63] Continuation of application No. PCT/EP97/06322, Nov. 12, 1997.

[30] Foreign Application Priority Data

Nov. 14, 1996 [EP] European Pat. Off. ............ 96 402 441

[51] Int. Cl.[7] .............................. A61K 38/09; C07K 7/23
[52] U.S. Cl. .............................. 514/15; 514/16; 530/313; 530/332; 930/130
[58] Field of Search ........................ 514/15, 16; 530/313, 530/322; 930/130

[56] References Cited

FOREIGN PATENT DOCUMENTS

| 0026640 | 4/1981 | European Pat. Off. . |
|---|---|---|
| 0413209 | 2/1991 | European Pat. Off. . |
| 98/21229 | 5/1998 | WIPO . |

OTHER PUBLICATIONS

Freidinger et al, "Bioactive Conformation of Luteinizing . . . Analog" Science, vol. 210, 1980, pp. 656–658 (XP 000670105).

Ward et al, "Potent and Highly Selective Neurokinin Antagonists" Jour. of Medic. Chem., vol. 33, No. 7, 1990, pp. 1848–1851 (XP 002029055).

Hinds et al, "Design and Synthesis . . . Beta–Turn Mimetic", J. Chem. Soc. No. 22, 1988, pp. 1447–1449 (XP 002029056).

Hinds et al, Synthesis, Conformational Properties . . . Derivatives: J. Med. Chem., vol. 34, 1991, pp. 1777–1789 (XP 0020229057).

Chalmers et al, "Pro–D–NMe–Amino Acid . . . Reverse–Turn Constraints" J. Am Chem. Soc, vol. 117, 1995, pp. 5927–5937 (XP 002029058).

*Primary Examiner*—Jeffrey E. Russel
*Attorney, Agent, or Firm*—Dennison, Scheiner, Schultz & Wakeman

[57] ABSTRACT

LH-RH analogues with excellent affinity for LH-RH receptors, of the formula $A_1\text{-}A_2\text{-}W\text{-}A_3\text{-}A_4\text{-}SPL\text{-}A_5\text{-}A_6\text{-}Pro\text{-}Z(I)$ in which:

- $-A_1$ is pGlu, AcSar or an aromatic D-amino acid;
- $-A_2$ is a direct bond, His, DPhe, DpFPhe or DpClPhe;
- *W is an aromatic L- or D-amino acid;
- $-A_3$ is Ala, Thr, Ser, DSer, Ser(OBzl) or MeSer;
- $-A_4$ is Tyr, Phe, cPzACAla, L- or D-PicLys, L- or D-NicLys or L- or D-IprLys;
- *SPL is the spirolactam of formula:

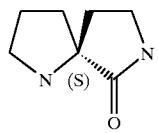

- $-A_5$ is an amino acid with a $(C_1\text{-}C_8)$alkyl or $(C_{3\text{-}C6})$ cycloalkyl side chain;
- $-A_6$ is L- or D-(Arg, HArg, Lys, HLys, Orn, Cit, HCit or Aph), where L- or D-(Arg and HArg) can be substituted by one or two $(C_1\text{-}C_4)$alkyl groups and L- or D-(Lys, HLys, Orn and Aph) can be substituted by an isopropyl, nicotinoyl or picolinoyl group; and
- *Z is $GlyNH_2$, $DAlaNH_2$, $AzaGlyNH_2$ or $-NHR_1$ where $R_1$ is a $(C_1\text{-}C_4)$alkyl optionally substituted by a hydroxy or one or several fluorine atoms, a $(C_3\text{-}C_6)$ cycloalkyl or a heterocyclic radical selected from the group consisting of morpholinyl, pyrrolidinyl and piperidyl;

or its pharmaceutically acceptable salts.

37 Claims, No Drawings

SEQUENCE LISTING

<160> NUMBER OF SEQ ID NOS: 34

<210> SEQ ID NO 1
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (2)
<223> OTHER INFORMATION: Xaa is His
<220> FEATURE:
<221> NAME/KEY: SITE
<222> LOCATION: (3)
<223> OTHER INFORMATION: Xaa is an aromatic L- or D-amino acid
<220> FEATURE:
<221> NAME/KEY: SITE
<222> LOCATION: (4)
<223> OTHER INFORMATION: Xaa is Ser
<220> FEATURE:
<221> NAME/KEY: SITE
<222> LOCATION: (5)
<223> OTHER INFORMATION: Xaa is Tyr
<220> FEATURE:
<221> NAME/KEY: SITE
<222> LOCATION: (6)
<223> OTHER INFORMATION: Xaa is a spirolactam
<220> FEATURE:
<221> NAME/KEY: SITE
<222> LOCATION: (7)
<223> OTHER INFORMATION: Xaa is an amino acid with a (C1-C8)alkyl side chain
<220> FEATURE:
<221> NAME/KEY: SITE
<222> LOCATION: (8)
<223> OTHER INFORMATION: Xaa is L- or D-Arg
<220> FEATURE:
<221> NAME/KEY: SITE
<222> LOCATION: (10)
<223> OTHER INFORMATION: Xaa is GlyNH2
<220> FEATURE:
<223> OTHER INFORMATION: Description of Artificial Sequence:LH-RH analogue

<400> SEQUENCE: 1

Xaa Xaa Xaa Xaa Xaa Xaa Xaa Xaa Pro Xaa
 1               5                  10

<210> SEQ ID NO 2
<211> LENGTH: 10
<212> TYPE: PRT
<213> ORGANISM: Homo sapiens
<220> FEATURE:
<221> NAME/KEY: SITE
<222> LOCATION: (1)
<223> OTHER INFORMATION: Xaa is pGlu

<400> SEQUENCE: 2

Xaa His Trp Ser Tyr Gly Leu Arg Pro Gly
 1               5                  10

```
<210> SEQ ID NO 3
<211> LENGTH: 10
<212> TYPE: PRT
<213> ORGANISM: Artificial Sequence
<220> FEATURE:
<221> NAME/KEY: SITE
<222> LOCATION: (6)
<223> OTHER INFORMATION: Xaa is a gamma-lactam
<220> FEATURE:
<223> OTHER INFORMATION: Description of Artificial Sequence:LH-RH
      analogue

<400> SEQUENCE: 3

Glu His Trp Ser Tyr Xaa Leu Arg Pro Gly
 1               5                  10

<210> SEQ ID NO 4
<211> LENGTH: 9
<212> TYPE: PRT
<213> ORGANISM: Artificial Sequence
<220> FEATURE:
<221> NAME/KEY: SITE
<222> LOCATION: (2)
<223> OTHER INFORMATION: Xaa is a spirolactam
<220> FEATURE:
<223> OTHER INFORMATION: Description of Artificial Sequence:nonapeptide

<400> SEQUENCE: 4

Tyr Xaa Tyr Asp Val Pro Asp Tyr Ala
 1               5

<210> SEQ ID NO 5
<211> LENGTH: 6
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Ava
<220> FEATURE:
<223> OTHER INFORMATION: Description of Artificial Sequence:
      [Ava6]-SP(6-11)

<400> SEQUENCE: 5

Xaa Phe Phe Gly Leu Met
 1               5

<210> SEQ ID NO 6
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (10)
<223> OTHER INFORMATION: Xaa is N-ethylamide
<220> FEATURE:
<223> OTHER INFORMATION: Description of Artificial Sequence:LH-RH
      analogue

<400> SEQUENCE: 6

Xaa His Trp Ser Tyr Xaa Leu Arg Pro Xaa
 1               5                  10
```

<210> SEQ ID NO 7
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is AcSar
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (10)
<223> OTHER INFORMATION: Xaa is N-ethylamide
<220> FEATURE:
<223> OTHER INFORMATION: Description of Artificial Sequence:LH-RH
      analogue

<400> SEQUENCE: 7

Xaa His Trp Ser Tyr Xaa Leu Arg Pro Xaa
 1               5                  10

<210> SEQ ID NO 8
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (3)
<223> OTHER INFORMATION: Xaa is 1Nal
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (10)
<223> OTHER INFORMATION: Xaa is N-ethylamide
<220> FEATURE:
<223> OTHER INFORMATION: Description of Artificial Sequence:LH-RH
      analogue

<400> SEQUENCE: 8

Xaa His Xaa Ser Tyr Xaa Leu Arg Pro Xaa
 1               5                  10

<210> SEQ ID NO 9
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (3)
<223> OTHER INFORMATION: Xaa is Nal
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (10)
<223> OTHER INFORMATION: Xaa is N-ethylamide
<220> FEATURE:

<223> OTHER INFORMATION: Description of Artificial Sequence:LH-RH
      analogue

<400> SEQUENCE: 9

Xaa His Xaa Ser Tyr Xaa Leu Arg Pro Xaa
 1               5                   10

<210> SEQ ID NO 10
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is AcSar
<220> FEATURE:
<221> NAME/KEY: SITE
<222> LOCATION: (3)
<223> OTHER INFORMATION: Xaa is Nal
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (10)
<223> OTHER INFORMATION: Xaa is N-ethylamide
<220> FEATURE:
<223> OTHER INFORMATION: Description of Artificial Sequence:LH-RH
      analogue

<400> SEQUENCE: 10

Xaa His Xaa Ser Tyr Xaa Leu Arg Pro Xaa
 1               5                   10

<210> SEQ ID NO 11
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (7)
<223> OTHER INFORMATION: Xaa is Npg
<220> FEATURE:
<221> NAME/KEY: SITE
<222> LOCATION: (10)
<223> OTHER INFORMATION: Xaa is N-ethylamide
<220> FEATURE:
<223> OTHER INFORMATION: Description of Artificial Sequence:LH-RH
      analogue

<400> SEQUENCE: 11

Xaa His Trp Ser Tyr Xaa Xaa Arg Pro Xaa
 1               5                   10

<210> SEQ ID NO 12
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE

```
<222> LOCATION: (6)
<223> OTHER INFORMATION: Xaa is as defined for SEQ ID NO:1
<220> FEATURE:
<221> NAME/KEY: SITE
<222> LOCATION: (7)
<223> OTHER INFORMATION: Xaa is Tle
<220> FEATURE:
<221> NAME/KEY: SITE
<222> LOCATION: (10)
<223> OTHER INFORMATION: Xaa is N-ethylamide
<220> FEATURE:
<223> OTHER INFORMATION: Description of Artificial Sequence:LH-RH
      analogue

<400> SEQUENCE: 12

Xaa His Trp Ser Tyr Xaa Xaa Arg Pro Xaa
 1               5                  10

<210> SEQ ID NO 13
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (7)
<223> OTHER INFORMATION: Xaa is Cha
<220> FEATURE:
<221> NAME/KEY: SITE
<222> LOCATION: (10)
<223> OTHER INFORMATION: Xaa is N-ethylamide
<220> FEATURE:
<223> OTHER INFORMATION: Description of Artificial Sequence:LH-RH
      analogue

<400> SEQUENCE: 13

Xaa His Trp Ser Tyr Xaa Xaa Arg Pro Xaa
 1               5                  10

<210> SEQ ID NO 14
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is AcDNal
<220> FEATURE:
<221> NAME/KEY: SITE
<222> LOCATION: (2)
<223> OTHER INFORMATION: Xaa is DpClPhe
<220> FEATURE:
<221> NAME/KEY: SITE
<222> LOCATION: (3)
<223> OTHER INFORMATION: Xaa is DTrp
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (10)
<223> OTHER INFORMATION: Xaa is DAlaNH2
<220> FEATURE:
<223> OTHER INFORMATION: Description of Artificial Sequence:LH-RH
      analogue

<400> SEQUENCE: 14
```

Xaa Xaa Xaa Ser Tyr Xaa Leu Arg Pro Xaa
 1               5                   10

<210> SEQ ID NO 15
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is AcDNal
<220> FEATURE:
<221> NAME/KEY: SITE
<222> LOCATION: (2)
<223> OTHER INFORMATION: Xaa is DpClPhe
<220> FEATURE:
<221> NAME/KEY: SITE
<222> LOCATION: (3)
<223> OTHER INFORMATION: Xaa is DPal
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (10)
<223> OTHER INFORMATION: Xaa is DAlaNH2
<220> FEATURE:
<223> OTHER INFORMATION: Description of Artificial Sequence:LH-RH
      analogue

<400> SEQUENCE: 15

Xaa Xaa Xaa Ser Tyr Xaa Leu Arg Pro Xaa
 1               5                   10

<210> SEQ ID NO 16
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is AcDNal
<220> FEATURE:
<221> NAME/KEY: SITE
<222> LOCATION: (2)
<223> OTHER INFORMATION: Xaa is DpClPhe
<220> FEATURE:
<221> NAME/KEY: SITE
<222> LOCATION: (3)
<223> OTHER INFORMATION: Xaa is DBal
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (10)
<223> OTHER INFORMATION: Xaa is DAlaNH2
<220> FEATURE:
<223> OTHER INFORMATION: Description of Artificial Sequence:LH-RH
      analogue

<400> SEQUENCE: 16

Xaa Xaa Xaa Ser Tyr Xaa Leu Arg Pro Xaa
 1               5                   10

<210> SEQ ID NO 17
<211> LENGTH: 10
<212> TYPE: PRT
<213> ORGANISM: Artificial Sequence
<220> FEATURE:
<221> NAME/KEY: SITE

```
<222> LOCATION: (1)
<223> OTHER INFORMATION: Xaa is AcDNal
<220> FEATURE:
<221> NAME/KEY: SITE
<222> LOCATION: (2)
<223> OTHER INFORMATION: Xaa is DpClPhe
<220> FEATURE:
<221> NAME/KEY: SITE
<222> LOCATION: (3)
<223> OTHER INFORMATION: Xaa is DPal
<220> FEATURE:
<221> NAME/KEY: SITE
<222> LOCATION: (5)
<223> OTHER INFORMATION: Xaa is IprLys
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (7)
<223> OTHER INFORMATION: Xaa is Npg
<220> FEATURE:
<221> NAME/KEY: SITE
<222> LOCATION: (10)
<223> OTHER INFORMATION: Xaa is DAlaNH2
<220> FEATURE:
<223> OTHER INFORMATION: Description of Artificial Sequence:LH-RH
      analogue

<400> SEQUENCE: 17

Xaa Xaa Xaa Ser Xaa Xaa Xaa Arg Pro Xaa
  1               5                  10

<210> SEQ ID NO 18
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is as defined for SEQ ID NO:1
<220> FEATURE:
<223> OTHER INFORMATION: Description of Artificial Sequence:LH-RH
      analogue

<400> SEQUENCE: 18

Xaa His Trp Ser Tyr Xaa Leu Arg Pro Gly
  1               5                  10

<210> SEQ ID NO 19
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is AcSar
<220> FEATURE:
<221> NAME/KEY: SITE
<222> LOCATION: (6)
<223> OTHER INFORMATION: Xaa is as defined for SEQ ID NO:1
<220> FEATURE:
<223> OTHER INFORMATION: Description of Artificial Sequence:LH-RH
      analogue

<400> SEQUENCE: 19

Xaa His Trp Ser Tyr Xaa Leu Arg Pro Gly
  1               5                  10
```

```
<210> SEQ ID NO 20
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (3)
<223> OTHER INFORMATION: Xaa is 1Nal
<220> FEATURE:
<221> NAME/KEY: SITE
<222> LOCATION: (6)
<223> OTHER INFORMATION: Xaa is as defined for SEQ ID NO:1
<220> FEATURE:
<223> OTHER INFORMATION: Description of Artificial Sequence:LH-RH
      analogue

<400> SEQUENCE: 20

Xaa His Xaa Ser Tyr Xaa Leu Arg Pro Gly
 1               5                  10

<210> SEQ ID NO 21
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (3)
<223> OTHER INFORMATION: Xaa is Nal
<220> FEATURE:
<221> NAME/KEY: SITE
<222> LOCATION: (6)
<223> OTHER INFORMATION: Xaa is as defined for SEQ ID NO:1
<220> FEATURE:
<223> OTHER INFORMATION: Description of Artificial Sequence:LH-RH
      analogue

<400> SEQUENCE: 21

Xaa His Xaa Ser Tyr Xaa Leu Arg Pro Gly
 1               5                  10

<210> SEQ ID NO 22
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (3)
<223> OTHER INFORMATION: Xaa is pClPhe
<220> FEATURE:
<221> NAME/KEY: SITE
<222> LOCATION: (6)
<223> OTHER INFORMATION: Xaa is as defined for SEQ ID NO:1
<220> FEATURE:
<223> OTHER INFORMATION: Description of Artificial Sequence:LH-RH
      analogue

<400> SEQUENCE: 22

Xaa His Xaa Ser Tyr Xaa Leu Arg Pro Gly
 1               5                  10
```

```
<210> SEQ ID NO 23
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (4)
<223> OTHER INFORMATION: Xaa is DSer
<220> FEATURE:
<221> NAME/KEY: SITE
<222> LOCATION: (6)
<223> OTHER INFORMATION: Xaa is as defined for SEQ ID NO:1
<220> FEATURE:
<223> OTHER INFORMATION: Description of Artificial Sequence:LH-RH
      analogue

<400> SEQUENCE: 23

Xaa His Trp Xaa Tyr Xaa Leu Arg Pro Gly
 1               5                  10

<210> SEQ ID NO 24
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (4)
<223> OTHER INFORMATION: Xaa is Ser(OBzl)
<220> FEATURE:
<221> NAME/KEY: SITE
<222> LOCATION: (6)
<223> OTHER INFORMATION: Xaa is as defined for SEQ ID NO:1
<220> FEATURE:
<223> OTHER INFORMATION: Description of Artificial Sequence:LH-RH
      analogue

<400> SEQUENCE: 24

Xaa His Trp Xaa Tyr Xaa Leu Arg Pro Gly
 1               5                  10

<210> SEQ ID NO 25
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (4)
<223> OTHER INFORMATION: Xaa is MeSer
<220> FEATURE:
<221> NAME/KEY: SITE
<222> LOCATION: (6)
<223> OTHER INFORMATION: Xaa is as defined for SEQ ID NO:1
<220> FEATURE:
<223> OTHER INFORMATION: Description of Artificial Sequence:LH-RH
      analogue

<400> SEQUENCE: 25

Xaa His Trp Xaa Tyr Xaa Leu Arg Pro Gly
 1               5                  10

<210> SEQ ID NO 26
```

```
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (10)
<223> OTHER INFORMATION: Xaa is AzaGlyNH2
<220> FEATURE:
<223> OTHER INFORMATION: Description of Artificial Sequence:LH-RH
      analogue

<400> SEQUENCE: 26

Xaa His Trp Ser Tyr Xaa Leu Arg Pro Xaa
 1               5                  10

<210> SEQ ID NO 27
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (7)
<223> OTHER INFORMATION: Xaa is Hol
<220> FEATURE:
<221> NAME/KEY: SITE
<222> LOCATION: (10)
<223> OTHER INFORMATION: Xaa is N-ethylamide
<220> FEATURE:
<223> OTHER INFORMATION: Description of Artificial Sequence:LH-RH
      analogue

<400> SEQUENCE: 27

Xaa His Trp Ser Tyr Xaa Xaa Arg Pro Xaa
 1               5                  10

<210> SEQ ID NO 28
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (7)
<223> OTHER INFORMATION: Xaa is Nle
<220> FEATURE:
<221> NAME/KEY: SITE
<222> LOCATION: (10)
<223> OTHER INFORMATION: Xaa is N-ethylamide
<220> FEATURE:
<223> OTHER INFORMATION: Description of Artificial Sequence:LH-RH
      analogue
```

<400> SEQUENCE: 28

Xaa His Trp Ser Tyr Xaa Xaa Arg Pro Xaa
 1               5                  10

<210> SEQ ID NO 29
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (2)
<223> OTHER INFORMATION: Xaa is DPhe
<220> FEATURE:
<221> NAME/KEY: SITE
<222> LOCATION: (6)
<223> OTHER INFORMATION: Xaa is as defined for SEQ ID NO:1
<220> FEATURE:
<223> OTHER INFORMATION: Description of Artificial Sequence:LH-RH
      analogue

<400> SEQUENCE: 29

Xaa Xaa Trp Ser Tyr Xaa Leu Arg Pro Gly
 1               5                  10

<210> SEQ ID NO 30
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (2)
<223> OTHER INFORMATION: Xaa is DPhe
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (10)
<223> OTHER INFORMATION: Xaa is DAlaNH2
<220> FEATURE:
<223> OTHER INFORMATION: Description of Artificial Sequence:LH-RH
      analogue

<400> SEQUENCE: 30

Xaa Xaa Trp Ser Tyr Xaa Leu Arg Pro Xaa
 1               5                  10

<210> SEQ ID NO 31
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is AcDNal
<220> FEATURE:
<221> NAME/KEY: SITE
<222> LOCATION: (2)
<223> OTHER INFORMATION: Xaa is DpClPhe
<220> FEATURE:
<221> NAME/KEY: SITE
<222> LOCATION: (3)
<223> OTHER INFORMATION: Xaa is DPal
<220> FEATURE:

```
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (7)
<223> OTHER INFORMATION: Xaa is Npg
<220> FEATURE:
<221> NAME/KEY: SITE
<222> LOCATION: (10)
<223> OTHER INFORMATION: Xaa is DAlaNH2
<220> FEATURE:
<223> OTHER INFORMATION: Description of Artificial Sequence:LH-RH
      analogue

<400> SEQUENCE: 31

Xaa Xaa Xaa Ser Tyr Xaa Xaa Arg Pro Xaa
 1               5                   10

<210> SEQ ID NO 32
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is AcDNal
<220> FEATURE:
<221> NAME/KEY: SITE
<222> LOCATION: (2)
<223> OTHER INFORMATION: Xaa is DpClPhe
<220> FEATURE:
<221> NAME/KEY: SITE
<222> LOCATION: (3)
<223> OTHER INFORMATION: Xaa is DPal
<220> FEATURE:
<221> NAME/KEY: SITE
<222> LOCATION: (5)
<223> OTHER INFORMATION: Xaa is NicLys
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (7)
<223> OTHER INFORMATION: Xaa is Npg
<220> FEATURE:
<221> NAME/KEY: SITE
<222> LOCATION: (10)
<223> OTHER INFORMATION: Xaa is DAlaNH2
<220> FEATURE:
<223> OTHER INFORMATION: Description of Artificial Sequence:LH-RH
      analogue

<400> SEQUENCE: 32

Xaa Xaa Xaa Ser Xaa Xaa Xaa Arg Pro Xaa
 1               5                   10

<210> SEQ ID NO 33
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is AcDNal
<220> FEATURE:
<221> NAME/KEY: SITE
<222> LOCATION: (2)
<223> OTHER INFORMATION: Xaa is DpClPhe
<220> FEATURE:
<221> NAME/KEY: SITE
<222> LOCATION: (3)
<223> OTHER INFORMATION: Xaa is DPal
```

```
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (7)
<223> OTHER INFORMATION: Xaa is Npg
<220> FEATURE:
<221> NAME/KEY: SITE
<222> LOCATION: (8)
<223> OTHER INFORMATION: Xaa is IprLys
<220> FEATURE:
<221> NAME/KEY: SITE
<222> LOCATION: (10)
<223> OTHER INFORMATION: Xaa is DAlaNH2
<220> FEATURE:
<223> OTHER INFORMATION: Description of Artificial Sequence:LH-RH
      analogue

<400> SEQUENCE: 33

Xaa Xaa Xaa Ser Tyr Xaa Xaa Xaa Pro Xaa
 1               5                  10

<210> SEQ ID NO 34
<211> LENGTH: 10
<212> TYPE: PRT
<213> ORGANISM: Artificial Sequence
<220> FEATURE:
<221> NAME/KEY: SITE
<222> LOCATION: (1)
<223> OTHER INFORMATION: Xaa is AcDNal
<220> FEATURE:
<221> NAME/KEY: SITE
<222> LOCATION: (2)
<223> OTHER INFORMATION: Xaa is DpClPhe
<220> FEATURE:
<221> NAME/KEY: SITE
<222> LOCATION: (3)
<223> OTHER INFORMATION: Xaa is DPal
<220> FEATURE:
<221> NAME/KEY: SITE
<222> LOCATION: (5)
<223> OTHER INFORMATION: Xaa is NicLys
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (7)
<223> OTHER INFORMATION: Xaa is Npg
<220> FEATURE:
<221> NAME/KEY: SITE
<222> LOCATION: (8)
<223> OTHER INFORMATION: Xaa is IprLys
<220> FEATURE:
<221> NAME/KEY: SITE
<222> LOCATION: (10)
<223> OTHER INFORMATION: Xaa is DAlaNH2
<220> FEATURE:
<223> OTHER INFORMATION: Description of Artificial Sequence:LH-RH
      analogue

<400> SEQUENCE: 34

Xaa Xaa Xaa Ser Xaa Xaa Xaa Xaa Pro Xaa
 1               5                  10
```

CONFORMATIONALLY CONSTRAINED LH-RH ANALOGUES, THEIR USES AND PHARMACEUTICAL COMPOSITIONS CONTAINING THEM

This application is a continuation of PCT/EP97/06322, filed Nov. 12, 1997.

This invention relates to LH-RH peptide analogues, to their use and to pharmaceutical compositions in which they are present.

LH-RH, or luteinizing hormone-releasing hormone, is a neurohumoral hormone produced in the hypothalamus which stimulates the secretion of the gonadotrophins, LH (luteinizing hormone) and FSH (follicle-stimulating hormone), which in turn regulate the endocrine and exocrine functions of the ovary in the female, and of the testis in the male. It has the following structural formula (SEQ ID NO: 2):

1 2 3 4 5 6 7 8 9 10 pGlu-His-Trp-Ser-Tyr-Gly-Leu-Arg-Pro-Gly-NH$_2$

Freidinger et al. (Science 1980, 210, 656–658) reports that an analogue of LH-RH containing a γ-lactam, of the formula (SEQ ID NO: 3):

Glu-His-Trp-Ser-Tyr-N(H)—[γ-lactam]—Arg-Pro-Gly-NH$_2$ shows to be 2.4 times as potent as LH-RH for inducing release of LH when tested in vivo in adult ovariectomized female rats primed with estradiol and progesterone.

Hinds et al. (J. Chem. Soc., Chem. Comm. 1988, 1447–1449) describes the synthesis of the spirolactam of the formula

A and its use in the construction by solid phase methods, of a conformationally locked analogue of the nonapeptide of the formula (SEQ ID NO: 4):

Tyr-A-Tyr-Asp-Val-Pro-Asp-Tyr-Ala

Ward et al. (J. Med. Chem. 1990, 33(7), 1848–1851) describe the substitution of the dipeptide residue -Gly-Leu- of the hexapeptide analogue [Ava$^6$]-SP(6–11) of substance P, of the formula (SEQ ID NO: 5):

6 7 8 9 10 11

Ava-Phe-Phe-Gly-Leu-Met-NH$_2$ by the spirolactam-containing group of the formula:

The hexapeptide analogue containing the (R) spirolactam is described as a full agonist at NK-1 receptors in guinea pig ileum longitudinal smooth muscle (GPI), while the hexapeptide analogue containing the (S) spirolactam shows no agonist activity in the GPI.

It has now been found that the introduction of the following spirolactam of (S) configuration:

(1)

in position 6 of the peptide chain of LH-RH and its analogues, produces compounds which display an excellent affinity for LH-RH receptors.

More specifically, the invention provides compounds which have a potent affinity for LH-RH receptors.

Thus, according to one aspect of the present invention, peptides are provided, of the formula (SEQ ID N° 1):

V-W-X-SPL-Y-Pro-Z (I)

in which:

* V is the peptide A$_1$A$_2$ in which:
  - A$_1$ is pGlu, AcSar or an aromatic D-amino acid such as DTrp, DPhe, DplPhe, DNal, AcDNal or DQal and
  - A$_2$ is a direct bond, His, DPhe, DpFPhe or DplPhe;
* W is an aromatic L-or D- amino acid such as Trp, DTrp, Nal, DNal, INal, Phe, DPhe, pClPhe, DpClPhe, Pal, DPal, Bal or DBal;
* X is the dipeptide A$_3$A$_4$ in which
  - A$_3$ is Ala, Thr, Ser, DSer, Ser(OBzl) or MeSer and
  - A$_4$ is Tyr, Phe, cPzACAla, L- or D-PicLys, L- or D-NicLys or L- or D-IprLys;
* SPL is the spirolactam (1) described above;
* Y is the dipeptide A$_5$A$_6$ in which
  - A$_5$ is an amino acid with a (C$_1$–C$_8$)alkyl or (C$_3$–C$_6$) cycloalkyl side chain, such as Ala, Abu, Aib, Val, Nva, Leu, Ile, Tle, Nle, Hol, Npg, CPa, Cba, Cpa or Cha and
  - A$_6$ is L- or D-(Arg, HArg, Lys, HLys, Orn, Cit, HCit or Aph), where L- or D-(Arg and HArg) can be substituted by one or two (C$_1$–C$_4$)alkyl groups and L- or D-(Lys, HLys, Orn and Aph) can be susbtituted by an isopropyl, nicotinoyl or picolinoyl group; and
* Z is GlyNH$_2$, DAIaNH$_2$, AzaGlyNH$_2$ or -NHR$_1$ where R$_1$ is a (C$_1$–C$_4$)alkyl optionally substituted by a hydroxy or one or several fluorine atoms; a (C$_3$–C$_6$) cycloalkyl or a heterocyclic radical selected from morpholinyl, pyrrolidinyl and piperidyl, as well as their pharmaceutically acceptable salts.

In the present description the term "(C$_1$–C$_4$)alkyl" denotes methyl, ethyl, n-propyl, i-propyl, n-butyl, i-butyl, s-butyl and t-butyl groups.

The term "(C$_1$–C$_8$)alkyl" denotes methyl, ethyl, n-propyl, i-propyl, n-butyl, i-butyl, s-butyl, t-butyl, n-pentyl, i-pentyl, s-pentyl, t-pentyl, hexyl, heptyl and octyl groups;

The term "(C$_3$–C$_6$)cycloalkyl" denotes cyclopropyl, cyclobutyl, cyclopentyl and cyclohexyl groups.

In the present description and in the claims, the following abbreviations are used:

Abu: 2-aminobutyric acid
AcDNal: acetyl D-3-(2-naphthyl)alanine
AcSar: acetylsarcosine
Aib: 2-aminoisobutyric acid
Ala: alanine
Aph: p-aminophenylalanine
Arg: arginine
AzaGlyNH$_2$: azaglycinamide
Bal: benzothienylalanine
Cba: cyclobutylalanine
Cha: cyclohexylalanine
Cit: citrulline
CPa: cyclopropylalanine
Cpa: cylopentylalanine
cPzACAla: cis-3-(4-pyrazinylcarbonylaminocyclohexyl)alanine
DAlaNH$_2$: D-alaninamide
DBal: D-benzothienylalanine
DNal: D-3-(2-naphthyl)alanine
DplPhe: D-3-(4-chlorophenyl)alanine
DpFPhe: D-3-(4-fluorophenyl)alanine
DPal: D-3-(3-pyridyl)alanine
DPhe: D-phenylalanine
DQal: D-3-(3-quinolyl)alanine
DSer: D-serine
DTrp: D-tryptophan
Gly: glycine
GlyNH$_2$: glycinamide
HArg: homoarginine
HCit: homocitrulline
His: histidine
HLys: homolysine
Hol: homoleucine
Ile: isoleucine
IprLys: N$^F$-isopropyllysine
Leu: leucine
Lys: lysine
MeSer: N-methylserine
Nal: 3-(2-naphthyl)alanine
1Nal: 3-(1-naphthyl)alanine
NEt: N-ethylamide
NicLys: N$^\epsilon$-nicotinoyllysine
Nle: norleucine
Npg: neopentylglycine
Nva: norvaline
OBzl: benzyl ester
Orn: ornithine
Pal: 3-(3-pyridyl)alanine
pClPhe: 3-(4-chlorophenyl)alanine
pGlu: pyroglutamic acid
Phe: phenylalanine
PicLys: Ng-picolinoyllysine
Pro: proline
Ser: serine
Thr: threonine
Tle: tert-leucine
Trp: tryptophan
Tyr: tyrosine
Val: valine A preferred group of peptides according to the invention, having LH-RH agonist activity, comprises the peptides of the formula:

V-W-X-SPL-Y-Pro-Z (IIa)

in which:
* V is the dipeptide A$_1$A$_2$ in which:
 -A$_1$ is pGlu or AcSar, and
 -A$_2$ is His;
* W is an aromatic L-amino acid such as Trp, Nal, lNal, Phe, Pal, Bal or pClPhe;
* X is the dipeptide A$_3$A$_4$ in which
 -A$_3$ is as defined above and
 -A4 is Tyr or Phe;
* SPL is as defined above;
* Y is the dipeptide A$_5$A$_6$ in which
 -A$_5$ is as defined above and
 -A$_6$ is Arg, Lys, HArg, HLys, Orn, Cit or HCit; and
* Z is GlyNH$_2$, AzaGlyNH$_2$ or -NHR$_1$ where R$_1$ is as defined above, and their pharmaceutically acceptable salts.

Another preferred group of peptides according to the invention, having LH-RH antagonist activity, comprises the peptides of the formula:

V-W-X-SPL-Y-Pro-Z (IIb)

in which:
* V is the peptide A$_1$A$_2$ in which:
 -A$_1$ is pGlu or an aromatic D-amino acid such as DTrp, DPhe, DplPhe, DNal, AcDNal or DQal; and
 -A$_2$ is a direct bond, DPhe, DpFPhe or DplPhe;
* W is Trp, DTrp, DPhe, DplPhe, DNal, DPal or DBal;
* X is the dipeptide A$_3$A$_4$ in which
 -A$_3$ is Ser and
 A$_4$ is Tyr, Phe, cPzACAla, L- or D-PicLys, L- or D-NicLys or L- or D-IprLys;
* SPL is as defined above;
* Y is the peptide A$_5$A$_6$ in which
 -A$_5$ is as defined above for (I) and
 -A$_6$ is as defined above for (I); and
* Z is GlyNH$_2$ or DAlaNH$_2$, and their pharmaceutically acceptable salts.

Among the peptides of formula (IIa), a preferred group comprises the peptides of the formula:

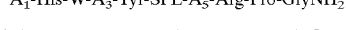
A$_1$-His-W-A$_3$-Tyr-SPL-A$_5$-Arg-Pro-GlyNH$_2$ (IIIa)

in which A$_1$, W, A$_3$ and A$_5$ are as defined above for (IIa).

Another preferred group of peptides (IIa) comprises the peptides of the formula:

A$_1$-His-W-Ser-Tyr-SPL-A$_5$-Arg-Pro-NEt (IVa)

in which $A_1$, W and $A_5$ are as defined above for (IIa).

A further preferred group of peptides (IIa) comprises the peptides of the formula:

$A_1$-His-W-Ser-Tyr-SPL-$A_5$-Arg-Pro-AzaGlyNH$_2$ (Va)

in which $A_1$, W and $A_5$ are as defined above for (IIa).

Among the peptides of formula (IIb), a preferred group comprises the peptides of the formula:

$A_1$-$A_2$-W-Ser-$A_4$-SPL-$A_5$-$A_6$-Pro-Z (II'b)

in which $A_1$, $A_2$, W, $A_4$, $A_5$, $A_6$ and Z are as defined above for (IIb).

A further preferred group of peptides (IIb) comprises the peptides of the formula:

$A_1$-$A_2$-W-Ser-Tyr-SPL-$A_5$-Arg-Pro-Z (IIIb)

in which $A_1$, $A_2$, $A_5$, W and Z are as defined above for (IIb).

Among the peptides (IIIa), those where $A_1$ is pGlu and $A_3$ is Ser are preferred. Also preferred are the peptides (IIIa) where $A_1$ is pGlu and W is Trp.

Among the peptides (II'b), those where $A_1$ is AcDNal, $A_2$ is DpClPhe, $A_5$ is Npg and Z is DAlaNH$_2$, are preferred.

Among the peptides (IIIb), those where $A_1$ is AcDNal, $A_2$ is DpClPhe and Z is DAlaNH$_2$ are preferred.

Especially preferred are the following peptides (SEQ ID NO: 6 to (SEQ ID NO: 17):

pGlu-His-Trp-Ser-Tyr-SPL-Leu-Arg-Pro-NEt
AcSar-His-Trp-Ser-Tyr-SPL-Leu-Arg-Pro-NEt
pGlu-His-1Nal-Ser-Tyr-SPL-Leu-Arg-Pro-NEt
pGlu-His-Nal-Ser-Tyr-SPL-Leu-Arg-Pro-NEt
AcSar-His-Nal-Ser-Tyr-SPL-Leu-Arg-Pro-NEt
pGlu-His-Trp-Ser-Tyr-SPL-Npg-Arg-Pro-NEt
pGlu-His-Trp-Ser-Tyr-SPL-Tle-Arg-Pro-NEt
pGlu-His-Trp-Ser-Tyr-SPL-Cha-Arg-Pro-NEt
AcDNal-DpClPhe-DTrp-Ser-Tyr-SPL-Leu-Arg-Pro-DAlaNH$_2$
AcDNal-DpClPhe-DPal-Ser-Tyr-SPL-Leu-Arg-Pro-DAlaNH$_2$
AcDNal-DpClPhe-DBal-Ser-Tyr-SPL-Leu-Arg-Pro-DAlaNH$_2$
AcDNal-DpClPhe-DPal-Ser-IprLys-SPL-Npg-Arg-Pro-DAlaNH$_2$

Examples of the salts with pharmaceutically acceptable acids are those with mineral acids, such as for example the hydrochloride, hydrobromide, sulfate, phosphate, borate, hydrogensulfate, dihydrogenphosphate or nitrate, and those with organic acids, such as for example the acetate, oxalate, tartrate, succinate, maleate, fumarate, gluconate, citrate, pamoate, malate, ascorbate, benzoate, p-toluenesulfonate or naphthalenesulfonate.

Examples of the salts with pharmaceutically acceptable bases are those with alkali or alkaline earth metals such as sodium, potassium, calcium or magnesium, and those with organic bases such as amines, trometamol, N-methylglutamine, and the like.

The peptides according to the present invention can be prepared by the well-known techniques of peptide chemistry such as for example peptide synthesis in solution or solid phase peptide synthesis. In general, these techniques involve the stepwise addition of one or more amino acids—which may be suitably protected—to a forming peptide chain.

Preferably, the peptides according to the invention are synthesized using stepwise solid phase synthesis (1,2) with N-α-Fmoc protection. For example, the peptides are assembled on a 4-methylbenzylhydrylamine resin (Peninsula Laboratories, UK) or on an aminomethyl resin (Peninsula Laboratories, UK). The C-terminal proline is introduced as 4-(Boc-Prolyloxymethyl)phenyl acetic acid. Subsequent removal of the Boc protecting group is achieved with trifluoroacetic acid followed by dichloromethane and dimethylformamide (DMF) washing as well as diisopropylethylamine neutralization. Also, it is possible to use a "Rink" resin, 4-(2',4'-dimethoxyphenyl)-Fmoc-aminomethylphenoxy resin using Fmoc/Boc strategy of synthesis (2).

The synthesis comprises assembling, cleavage and purification steps, as described below:

I. Assembling

For all the peptides the following deprotection/coupling procedure is used:

1—DMF washing (3 times—1 min.)
2—Piperidine 25% in DMF (1 min.)
3—Piperidine 25% in DMF (twice—15 min.)
4—DMF washing (7 times—1 min.)

For each step 15 ml of solvent per gram of peptide resin are used.

Coupling of all the amino acids (three fold excess) is performed in DMF in the presence of BOP, HoBt and DIEA (3). Each coupling step is controlled for completion by the ninhydrine test (4) and double coupling is performed if necessary. If, after the second coupling the test still remains positive, the resin is acetylated (acetic acid anhydride, 10 fold excess and DIEA).

Generally, a trifluoroacetic acid (TFA) treatment is performed prior to the deprotection/cleavage step.

II. Cleavage

The peptides are cleaved from the resin and fully deprotected by a treatment with liquid hydrogen fluoride (HF). 10 ml of HF per gram of peptide resin are used classically at 0° C. for 45 min. in the presence of p-cresol and ethanedithiol (for tryptophan-containing peptides) as scavengers.

After evaporation of the HF, the crude reaction mixture is washed with diethyl ether, dissolved in TFA, precipitated with diethyl ether and dried under reduced pressure.

If need be, prior to HF deprotection the peptide is cleaved from the resin and subsequently amidated by a treatment with ethylamine (5 ml ethylamine per gram of petpide resin, −78° C., 20 hours).

When a benzyl group is present in the final product, TFA is used (10 ml per gram of peptide resin, 0° C., 2,5 hours) for the final cleavage/deprotection.

The composition of the cleavage mixture in v % is the following:

TFA:83.3%

Ethanedithiol: 2.1%

Thioanisol: 4.2%

Water:4.2%

Phenol: 6.2%

After filtration of the resin, the peptide is precipitated from the reaction mixture by addition of a large amount of diethylether. After several washings with diethylether the crude peptide is dried under reduced pressure.

III. Purification

All the peptides are purified by reverse phase liquid chromatography.

The general procedure of purification is identical for each peptide however the gradient of organic solvent is adjusted depending on the initial retention time of the peptide.

General conditions of purification:

Equipment: KRONWALD SPERATIONSTECHNIK, Medium

Pressure liquid chromatography system (Germany) equipped with Glass column.

Stationary phase: silica Bondapack C 18 (Waters) 15–25 µm, 100 A

Size of column: 40×340 mm

Elution conditions: Mobile phase: Eluant A: 0.1% TFA in water

Eluant B: $CH_3CN/A$ 60/40 (volume)

Temperature: Room

Flow rate: 40 ml

Detection: UV 210 nm

Fractioning: 5 ml per fraction

All fractions containing the target compound are individually analyzed by analytical HPLC. The fractions with a purity higher than 95% are pooled and freeze-dried. In case the requested purity is not reached after the first purification step, a second purification step and, if need be, a third purification step are performed. The conditions of purification for the second and third steps are similar as those described above except that the slope of the gradient is modified in order to increase the resolution.

After lyophilisation, all purified peptides are present as their trifluoroacetate salt. The final powder corresponding to each peptide is controlled by analytical HPLC. The structure of each compound is also assessed by mass spectral analysis and the net peptide content is determinated by UV absorption.

The peptides according to the present invention have a potent affinity for the LH-RH receptors.

This affinity has been determined according to the following method:

Pituitaries from female Sprague Dawley rats were removed and homogenized with a Potter homogenizer in a 25 mM HEPES buffer (pH 7.4) containing 0.32 M sucrose, 100 µg/l PMSF (phenylmethylsulfonylfluoride), 5.6 U/l aprotinin and 10,000 U/l bacitracin. The homogenates were centrifuged at 700 g for 10 minutes and the supernatants were further centrifuged at 12,500 g for 30 minutes. The pellets were homogenized and centrifuged as described above, in the same buffer but without sucrose.

All homogenization, centrifugation and subsequent incubation steps were carried out at 4° C.

Aliquots of membrane fractions were incubated for 2 hours in duplicate with increasing concentrations of test compounds in the presence of 20 to 70 µM of [$^{125}$I]-buserelin (between 1000 and 2000 Ci/mmol depending on ligand batches). The assay was terminated by filtration under suction (Brandel 96-well harvester) through Whatman GF/B glass fiber filters. After repeated washes, filters were placed in counting vials with scintillation cocktail to measure the radioactivity of $^{125}$I. For each experiment, curve-fitting of residual specific binding against concentrations of test compound gave the 50% inhibitory concentration ($IC_{50}$). Each compound was tested in at least 4 experiments.

This LH-RH receptor assay was characterized by 4 saturation experiments using increasing concentration of [$^{125}$I]-buserelin in the absence or presence of 1 µM unlabelled buserelin for non specific binding determination. Specific binding data were analysed according to Scatchard's method. At equilibrium (2 hours of incubation), the dissociation constant (Kd) and the number of binding sites for [$^{125}$I]-buserelin were respectively equal to 88±6 pM and 15.6±2.9 pM.

For each test compound, the inhibitory constant (Ki) was calculated from its $IC_{50}$ according to the Cheng and Prussofs equation: $Ki=IC_{50}/(1+[radioligand]/Kd)$. Ki was then transformed into pKi (=–log Ki) for final expression of affinity scales.

The natural ligand, LH-RH itself, displays a strong affinity with experimental $IC_{50}$ in the 10 nM range, i.e., a pKi equal to about 8.

So-called superagonists like buserelin, leuprorelin, tryptorelin, histrelin or deslorelin and antagonists like antide show an even stronger binding to LH-RH receptors with $IC_{50}$ in the subnanomolar range, i.e. pKi>9.

The affinity of test peptides of the invention for the LH-RH receptors is given in Table I below:

TABLE 1

| Affinity for LH-RH receptors | |
|---|---|
| Compound | pKi |
| Example 9 | 8.94 |
| Example 10 | 8.21 |
| Example 11 | 9.37 |
| Example 12 | 9.98 |
| Example 13 | 8.98 |
| Example 15 | 8.64 |
| Example 16 | 9.26 |
| Example 17 | 8.75 |
| Example 18 | 8.69 |
| Example 19 | 9.43 |
| Example 20 | 8.39 |
| Example 21 | 8.01 |
| Example 22 | 9.05 |
| Example 23 | 9.81 |
| Example 24 | 9.60 |
| Example 25 | 9.61 |
| Example 26 | 9.58 |
| Example 27 | 10.01 |
| Example 28 | 9.51 |
| Example 29 | 9.44 |
| LH-RH | 8.04 |
| Leuprorelin | 9.33 |
| Tryptorelin | 9.85 |
| Goserelin | 8.58 |
| Deslorelin | 9.90 |
| Buserelin | 9.37 |
| Histrelin | 9.98 |
| Antide | 9.22 |

The peptides according to the general formula (IIa) exert an agonist activity upon the LH-RH receptors in vivo, resulting in the induction of ovulation in the female and in the stimulation of testosterone secretion in the male following acute subcutaneous administration.

Adult female Wistar rats are first monitored for normal estrous cyclicity by daily vaginal smears. After at least 2 regular 4-day cycles, they all receive an intraperitoneal injection of 50 mg/kg of sodium pentobarbital around 2:00 PM on the day of proestrus, which blocks the spontaneous ovulation in the negative control animals receiving in addition only the subcutaneous vehicle (PBS: phosphate buffered saline, 0.05 M, pH 7.4 containing 0.1% bovine serum albumin). At the same time, test animals are injected subcutaneously with LH-RH, standard LH-RH agonists or examples according to the formula (Ha), at various doses in solution in the vehicle described above. The following morning, the oviducts are excised and carefully dissected to search for ovocytes. None are found in the negative pentobarbital-blocked animals.

If effective, LH-RH agonists induce ovulation during the night between proestrus and estrus. The percentage of ovulating female rats, defined by the presence of at least one ovocyte in one of the two oviducts, is plotted as a function of the injected dose. The potency of LH-RH and agonists is expressed by the dose producing 50% of ovulation ($ED_{50}$) among experimental groups comprising between 6 to 12 animals.

The in vivo potency of test peptides according to formula (IIa) to induce ovulation is given in Table 2 below:

TABLE 2

Induction of ovulation

| Compound | $ED_{50}$ (nanograms/rat) |
|---|---|
| Example 9 | 3.5 |
| Example 10 | 5.0 |
| Example 12 | 4.6 |
| LH-RH | 15 |
| Leuprorelin | 1.9 |
| Tryptorelin | 2.9 |
| Goserelin | 4.3 |
| Deslorelin | 4.8 |

Adult male Sprague-Dawley rats are treated by a subcutaneous injection of LH-RH agonists at the same dose of 30 nanograms/kg dissolved in PBS. Two hours later, blood samples are drawn for total plasma testosterone measurement by direct radioimmunoassay (Immunotech). At this dose, LH-RH itself is not active standard LH-RH agonists and selected examples according to formula (IIa) are compared in Table 3 below:

TABLE 3

Total testosterone

| Compound | Total testosterone (ng/ml) | n (animals per group) |
|---|---|---|
| Example 9 | 13.1 ± 1.0*** | 6 |
| Example 10 | 9.5 ± 3.1** | 5 |
| Example 11 | 11.4 ± 2.7** | 5 |
| Example 17 | 9.1 ± 1.3*** | 6 |
| Example 18 | 7.3 ± 1.6** | 6 |
| Example 19 | 11.7 ± 1.1*** | 6 |
| Buserelin | 15.4 ± 0.71*** | 23 |
| Goserelin | 15.0 ± 2.5*** | 6 |
| Histrelin | 12.7 ± 1.9*** | 6 |
| Tryptorelin | 12.1 ± 0.7*** | 6 |
| Leuprorelin | 11.9 ± 1.5*** | 6 |
| Vehicle (PBS) | 2.28 ± 0.40 | 23 |

**$p < 0.01$
***$p < 0.001$

The peptides according to the general formula (IIb) exert an antagonist activity upon the LH-RH receptors in vivo, resulting in the inhibition of ovulation in the female.

Adult female Wistar rats are first monitored for normal estrous cyclicity by daily vaginal smears. After at least 2 regular 4-day cycles, they received by subcutaneous injection either the vehicle alone (0.5 ml of a mixture of propylene-glycol and water: 20/80 vol/vol), or the LH-RH antagonist according to the formula (IIb) dissolved in this vehicle, around 2:00 PM on the day of proestrus. All but one vehicle-treated animals ovulated spontaneously as demonstrated by the recovery of numerous ovocytes in the oviducts the following morning.

If effective, LH-RH antagonists totally block ovulation. An antagonist activity was detected with e.g. the compounds of examples 23, 25, 26, 27, 28 and 29. The 50% inhibitory dose of antide is slightly lower than 1 μg/rat. At this dose the compound of example 26 is still active, although with a lower intensity. The compound of example 27 does however appear to be more potent than antide in this set of experiments.

TABLE 4

Inhibition of ovulation

| Treatment | Dose (μg/rat) | Number of ovulating females/ total number of treated females |
|---|---|---|
| Vehicle | — | 29/30 |
| Antide | 10 | 0/8 |
|  | 5 | 0/11 |
|  | 2.5 | 2/6 |
|  | 1 | 5/16 |
|  | 0.5 | 4/5 |
| Example 23 | 10 | 1/5 |
|  | 5 | 6/6 |
| Example 25 | 5 | 2/5 |
| Example 26 | 5 | 1/5 |
|  | 1 | 3/5 |
| Example 27 | 5 | 0/5 |
|  | 1 | 0/5 |
|  | 0.5 | 3/5 |
| Example 28 | 5 | 2/5 |
| Example 29 | 5 | 0/5 |
|  | 1 | 5/5 |

No sign of toxicity is observed with the peptides of the invention at pharmaceutically active doses.

Thus, the peptides of the invention and their pharmaceutically acceptable salts may be used in the treatment or prevention of various complaints or diseases wherein a LH-RH agonist or antagonist activity is required.

The main target of LH-RH analogues is the pituitary gland, but direct actions have been reported on the gonads themselves (testis and ovary), on the thymus and some lymphoid cell lines, on mast cells and on breast, prostate or pancreatic tumors.

LH-RH agonists according to formula (IIa) exert on any LH-RH sensitive target, either a stimulatory activity by short-term acute or pulsatile administrations, or an inhibitory effect by repeated or continuous administrations that induce the desensitization and the down-regulation of LH-RH receptors. In the case of the hypothalamo-pituitary-gonadal axis, prolonged administration results in a so-called "chemical" castration.

LH-RH antagonists according to formula (IIb) exert primarily an inhibitory effect on any LH-RH-sensitive target, but are also useful in obtaining or planning a rebound stimulatory release of LH and FSH when treatment is discontinued.

Due to this ambivalent potential of both LH-RH agonists and antagonists, all analogues according to formula (I) can find an appropriate therapeutic use in humans as well as in animals, depending on doses, treatment regimens and routes of administration, in reproductive endocrinology and in the treatment or prevention of sex hormone-dependent benign or malignant tumors, alone or in combination with other hormonal or antitumoral agents. LH-RH sensitive sex hormone-independent benign or malignant tumors can also regress upon treatment with LH-RH analogues according to formula (I), alone or in combination with antitumoral agents. Immune mechanisms can also be modified by LH-RH analogues according to formula (I), alone or in combination with immuno-modulating or -suppresive agents such as glucocorticoids, cyclosporin, rapamycin, tacrolimus, their derivatives, and the like. The LH-RH analogues according to the invention are therefore very valuable in the treatment and prevention of autoimmune diseases, graft rejection or atopic diseases, and in the treatment of benign or malignant lymphoproliferative disorders.

LH-RH analogues according to formula (I) are especially useful, alone or in combination with sex steroids or gonadotrophins, in the inhibition, planning and triggering of ovulation in in vitro fertilization programs, and in the treatment of male and female infertility or hypogonadic states. Conversely, they can also be used in male or female contraception or treatment of hypergonadic states, alone or in combination with sex steroids or gonadotrophins. This applies to men and women, but also to wild or domestic animals in uses such as improvement or control of reproductive performance, or as a tool to optimize breeding strategies.

LH-RH analogues according to formula (I) are also especially useful in men to treat advanced prostate cancer, but can also be used as a first line therapy in this indication and in benign prostatic hypertrophy, alone or in combination with inhibitors of androgen action, i.e. the antiandrogens such as cyproterone acetate, osaterone acetate, chlormadinone acetate, flutamide, nilutamide or bicalutamide and the like, or with 5α-reductase inhibitors such as finasteride, epristeride or turosteride and the like, or else with $C_{17-20}$ lyase inhibitors such as abiraterone and the like.

LH-RH analogues according to formula (I) are also especially useful in the treatment or prevention of breast cancer in women and in men, especially estrogen receptor positive tumors, alone or in combination with antiestrogens such as tamoxifen, raloxifen or droloxifen and the like, or with aromatase inhibitors such as atamestane, formestane, letrozole, anastrozole and the like or else with $C_{17-20}$ lyase inhibitors such as abiraterone and the like, but also of certain estrogen receptor negative tumors that respond to the direct effects of LH-RH analogues or indirectly to their gonadal suppressive activity.

Other gynecological conditions, such as endometrial hyperplasia, leiomyoma, adenomyoma, endometriosis, polycystic ovary syndrome, hirsutism and benign breast disease (pain, cysts or fibrosis), can also be prevented by or benefit from treatment with the LH-RH analogues according to formula (I), alone or in combination with antiestrogens (cited above), progestins such as cyproterone acetate, osaterone acetate, chlormadinone acetate, nomegestrol acetate, promegestone, demegestone, trimegestone and the like, or their contraceptive or post-menopausal replacement combination formulations with estrogens such as estradiol or ethynylestradiol. The peptides of the invention can also interfere with gestation by inducing abortion or by triggering labor, alone or in combination with estrogens (cited above), antiprogestins such as mifepristone or prostaglandin analogs such as sulprostone.

Similar indications can be encountered in veterinary medicine for male or female domestic or wild animals that may require the use of LH-RH analogues according to formula (I).

Another aspect of the present invention is therefore pharmaceutical compositions containing an effective amount of at least one peptide of formula (I) or a pharmaceutically acceptable salt thereof, alone or mixed with suitable pharmaceutical excipients.

A further aspect of the invention relates to a method of treating and/or preventing the above diseases which comprises administering to patients or animals in need thereof a therapeutically effective amount of a peptide of formula (I) or a pharmaceutically acceptable salt thereof.

A further aspect of the invention relates to the use of the peptides of formula (IIa), or of their pharmaceutically acceptable salts, for the preparation of a medicament having LH-RH agonist activity. Also within the scope of the invention is the use of the peptides of formula (IIb), or of their pharmaceutically acceptable salts, for the preparation of a medicament having LH-RH antagonist activity.

The peptides of the invention are preferentially administered by parenteral administration, although oral formulations are also effective provided that the dosage is appropriately increased.

Preferred delivery systems for LH-RH agonists of formula (IIa) in long term pituitary-gonadal suppressive indications are slow-release implantable devices, or injectable biodegradable polymeric micro- or nano-particles or -capsules, or micro- or nano-emulsions, with unit doses of the peptides or of their appropriate salts ranging from 1 mg to 100 mg per human patient for a duration of action ranging from 1 month to 1 year. Long term administration of LH-RH antagonists of formula (IIb) will generally require higher dosages in the same slow-release formulations, ranging from 10 mg to 1 g for 1 week to 1 year of activity. Animal doses will be adapted on a body weight basis depending on the wild or domestic species to be treated either by LH-RH agonists or antagonists according to formula (I).

All other means of parenteral administration are suited for immediate, delayed or planned delivery of the peptides of the invention subcutaneous, intramuscular, intravenous, intragonadal or intratumoral needle bolus injections, or prolonged continuous, pulsatile or planned perfusions or microinfusions using the appropriate pump technology; gas-propelled subcutaneous microinjection; vaginal creams, gels or pessaries; rectal enemas or suppositories; transdermal creams, gels, lotions, solutions, patches or iontophoretic devices; nasal spray or dry powder inhalation device; ophthalmic solutions, gels, creams or contact lenses; pulmonary inhalation of micro- or nano-particles or droplets generated manually or with an appropriate pulverization device.

The unit dose of these parenteral administrations will range in humans from 0.001 mg to 10 mg/day for LH-RH agonists of formula (IIa) and from 0.01 to 100 mg/day for LH-RH antagonists of formula (IIb), one to 16 times per day (in the case of pulsatile administration).

Oral administration of peptides according to the invention is preferentially effected using gastro-resistant and delayed enteric or colonic release formulations which can be coated pills or tablets containing two or more components, hardened gelatin capules, special polymeric macro-, micro- or nano-beads containing them, or any device designed to protect them from gastrointestinal degradation and to release them when needed. All other formulations to be taken orally such as solutions, suspensions, syrups, gels and the like, or lingual, sublingual or chewable formulations are suited provided that the dosage is increased.

Overall, effective oral treatment may be achieved with any of the above formulations with unit doses of peptides of formula (I) ranging from 1 mg to 1 g per human patient, from one to 16 times per day (in the case of pulsatile administration).

All the above-mentioned oral or parenteral formulations of the peptides according to the invention and their pharmaceutical acceptable salts may contain one or several pharmaceutically appropriate excipients, one or several inhibitors of proteases, and one or several absorption enhancers as needed by the specific route of administration.

Raw powder of pure peptides according to the invention or their pharmaceutically acceptable salts can also be used, especially in the lyophilized form for fast sublingual application.

The invention will now be described with reference to the following examples, which are not intended to limit the invention in any respect. In these examples, the starting materials used were either commercially available or synthetized, as mentioned below:

-Fmoc-Glu-OH, Fmoc-Tyr(OBut)-OH, Fmoc-Trp-OH and Fmoc-His(Trt) were purchased from Propeptide (France).

-Fmoc-Trp(Boc) was purchased from Novabiochem (Switzerland).

-Fmoc-Sarcosine and Fmoc-D-Ser(OBut)-OH were purchased from Bachem (Switzerland).

-Fmoc-Arg(Tos)-OH, Fmoc-Tyr(2-Br-Z)-OH and Fmoc-Ser(Bzl)-OH were synthesized according to Bodanszky and Bodanszky (5) starting from the corresponding Boc-protected amino acid.

-Fmoc-β-1-Nal-OH, Fmoc-β-Nal-OH and Fmoc-pClPhe were synthesized as racemates.

The corresponding acetyl ethylesters were enzymatically resolved using subtilisin (6).

-MeSer was synthesized according to Mc Dermott and Benoiton (7).

-Fmoc-(S)SPL-Leu-OH was synthesized according to Hinds et al (8) and Ward et al (9).

EXAMPLE 1

(SEQ ID NO: 18): pGlu-His-Trp-Ser-Tyr-SPL-Leu-Arg-Pro-Gly-$NH_2$

Assembling and cleavage of the peptide were carried out as described for Example 2. 532 mg of crude product were obtained. Purification was carried out using a linear gradient of from 35 to 50% of eluent B ($CH_3CN$/0.1% TFA 60/40 v/v) over 30 min. 56 mg (approximate yield 11%) of purified material were obtained.

Mass spectral analysis—$ES^+$ mode:
expected: 1248.4
found: 1248.1 (average).
net peptide content 73.4%; purity 96.4%; retention time 11.62 min.

EXAMPLE 2

(SEQ ID NO: 19): AcSar-His-Trp-Ser-Tyr-SPL-Leu-Arg-Pro-Gly-$NH_2$

The synthesis was carried out at a 1.2 mmole scale. After addition of the tyrosine, the peptide resin was split into approximately 6 parts for assembling of the corresponding sequences.

Starting with 4-methylbenzylhydrylamine resin, glycine, proline and arginine were coupled using a t-Boc strategy as described above in the general synthesis of the invention peptides. SPL-Leu and tyrosine were introduced using N-α-Fmoc protection.

After the tyrosine, the subsequent amino acids were coupled using a Fmoc strategy as described. Prior to the final HF cleavage a TFA treatment was performed to remove the t-Butyl side-chain protecting groups.

Purification was carried out using a linear gradient of from 15 to 70% of eluent B over 30 min. After lyophilisation 57 mg (approximate yield 39 %) of purified material were obtained.

Mass spectral analysis—$FAB^+$ mode:
expected value: 1250.58 (average)
found: 1250.5 (MH+).
net peptide content 73.7%; purity 97.1%; retention time 18.38 min.

EXAMPLE 3

(SEQ ID NO: 20): pGlu-His-1Nal-Ser-Tyr-SPL-Leu-Arg-Pro-Gly-$NH_2$

Assembling and cleavage of the peptide were carried out as described for Example 2.

Purification was carried out using a linear gradient of from 25 to 75% of eluent B over 30 min.

54 mg (approximate yield 13%) of purified material were obtained.

Mass spectral analysis—$FAB^+$ mode:
expected: 1959.6
found: 1959.4 ($MH^+$)
net peptide content 84.6%; purity 95.3%; retention time 14.18 min.

EXAMPLE 4

(SEQ ID NO: 21): pGlu-His-Nal-Ser-Tyr-SPL-Leu-Arg-Pro-Gly-$NH_2$

Assembling and cleavage of the peptide were carried out as described for Example 2.

Purification was carried out using a linear gradient of from 30 to 60% of eluent B over 30 min.

68 mg (approximate yield 25%) of purified material were obtained.

Mass spectral analysis—$FAB^+$ mode:
expected: 1259.6
found: 1259.4 ($MH^+$)
net peptide content 81.8%; purity 99.2%; retention time 14.20 min.

EXAMPLE 5

(SEQ ID NO: 22): pGlu-His-pClPhe-Ser-Tyr-SPL-Leu-Arg-Pro-Gly-$NH_2$

Assembling and cleavage of the peptide were carried out as described for Example 2.

Purification was carried out in two steps, the first one using a linear gradient of from 10 to 70% of eluent B over 30 min. and the second one using a linear gradient of from 10 to 70% of eluent B over 40 min.

50 mg (approximate yield 19%) of purified material were obtained.

Mass spectral analysis—$FAB^+$ mode:
expected: 1244.0
found: 1243.5 ($MH^+$)
net peptide content 73.8%; purity 97.2%; retention time 13.65 min.

EXAMPLE 6

(SEQ ID NO: 23): pGlu-His-Trp-DSer-Tyr-SPL-Leu-Arg-Pro-Gly-$NH_2$

Assembling and cleavage of the peptide were carried out as described for Example 2.

Purification was carried out using a linear gradient of from 30 to 50% of eluent B over 30 min.

75 mg (approximate yield 27%) of purified material were obtained.

Mass spectral analysis—$FAB^+$ mode:
expected: 1248.3
found: 1248.5 ($MH^+$)
net peptide content 68.1%; purity 98.6%; retention time 17.78 min.

EXAMPLE 7

(SEQ ID NO: 24):pGlu-His-Trp-Ser(OBzl)-Tyr-SPL-Leu-Arg-Pro-Gly-$NH_2$

The peptide was synthesised by solid phase synthesis using a Fmoc/Boc strategy as described above in the general synthesis of the invention peptides.

The serine residue was introduced as Fmoc-Ser(OBzl).

Cleavage was performed with TFA in the presence of a scavenger as described. 0.328 g (wet weight) of crude product was obtained.

Purification was carried out using a linear gradient of from 25 to 80% of eluent B over 30 minutes. After lyophilisation 82 mg (31% yield) of purified peptide were obtained.

Mass spectral analysis: FAB+ mode:
expected: 1338.4 (average)
found: 1338.5 (MH+).
net peptide content 78.3%; purity 96.0%; retention time 16.17 min.

EXAMPLE 8
(SEQ ID NO: 25): pGlu-His-Trp-MeSer-Tyr-SPL-Leu-Arg-Pro-Gly-NH2

Assembling and cleavage of the peptide were carried out as described for Example 2.

Purification was carried out in 3 steps, the first and second ones using a linear gradient of from 20 to 70% of eluent B over 30 min., and the third one using a linear gradient of from 30 to 50% of eluent B over 30 min.

15 mg (approximate yield 4%) of purified material were obtained.

Mass spectral analysis—FAB+ mode
expected: 1262.5
found: 1262.3 (MH+)
net peptide content 68.6%; purity 96.3%; retention time 18.58 min.

EXAMPLE 9
(SEQ ID NO: 6): pGlu-His-Trp-Ser-Tyr-SPL-Leu-Arg-Pro-NEt

The synthesis was carried out on Boc-Pro-PAM resin, the second amino acid, arginine, was also incorporated via a t-Boc strategy as described above in the general synthesis of the invention peptides.

The subsequent amino acids were incorporated via a Fmoc strategy as described above.

After coupling of the N-terminal amino acid, the peptide was cleaved from the resin and converted into ethylamide by aminolysis using ethylamine (5 ml of ethylamine per gram of peptide resin for 20 hours, −78° C.).

After cleavage the protected peptide was extracted with methanol, dried and deprotected with HF as described above.

Purification was carried out in two steps, the first one using a linear gradient of from 30 to 50% of eluent B over 30 min., and the second one using a linear gradient of from 25 to 45% of eluent B over 30 min.

19 mg (approximate yield 8%) of purified material were obtained.

Mass spectral analysis—FAB+ mode:
expected: 1219.4
found: 1219.6 (MH+)
net peptide content 72.5%; purity 95.2%; retention time 10.28 min.

EXAMPLE 10
(SEQ ID NO: 7): AcSar-His-Trp-Ser-Tyr-SPL-Leu-Arg-Pro-NEt

Assembling and cleavage of the peptide were carried out as described for example 9.

Purification was carried out using a linear gradient of from 20 to 70% of eluent B over 30 min.

24 mg (approximate yield 22%) of purified material were obtained.

Mass spectral analysis—FAB+ mode:
expected 1221.4
found: 1221.6 (MH+)
net peptide content 83.5%; purity 96.1%; retention time 15.85 min.

EXAMPLE 11
(SEQ ID NO: 8): pGlu-His-INal-Ser-Tyr-SPL-Leu-Arg-Pro-NEt

Assembling and cleavage of the peptide were carried out as described for example 9.

Purification was carried out using a linear gradient of from 20 to 70% of eluent B over 30 min.

33 mg (approximate yield 20%) of purified material were obtained.

Mass spectral analysis—ES+ mode:
expected: 1229.5
found: 1229.9 (average)
net peptide content 80.6%; purity 97.9%; retention time 14.85 min.

EXAMPLE 12
(SEQ ID NO: 9): pGlu-His-Nal-Ser-Tyr-SPL-Leu-Arg-Pro-NEt

Assembling and cleavage of the peptide were carried out as described for example 9.

Purification was carried out using a linear gradient of from 40 to 60% of eluent B over 30 min.

21 mg (approximate yield 28%) of purified material were obtained.

Mass spectral analysis—ES+ mode:
expected: 1229.5
found: 1230.1 (average)
net peptide content 74.7%; purity 95.2%; retention time 14.80 min.

EXAMPLE 13
(SEQ ID NO: 26): AcSar-His-Nal-Ser-Tyr-SPL-Leu-Arg-Pro-NEt

Assembling and cleavage of the peptide were carried out as described for example 9.

Purification was carried out using a linear gradient of from 20 to 80% of eluent B over 30 min.

36 mg (approximate yield 15%) of purified material were obtained.

Mass spectral analysis—ES+ mode:
expected: 1232.5
found: 1232.2 (average)
net peptide content 68.9%; purity 95.1%; retention time 13.48 min.

EXAMPLE 14
pGlu-His-Trp-Ser-Tyr-SPL-Leu-Arg-Pro-AzaGly-NH$_2$

The peptide was synthesized by solid phase synthesis on a Rink resin.

The C-terminal AzaGly-NH$_2$ was generated as follows: to 1.9 g of deprotected Rink resin, 0.55 g (3 eq.) of p-nitrophenylchloroformate was added in DCM at −78° C. in the presence of DIEA (3 eq.). The reaction mixture was stirred at RT for 48 h and the resin was then thoroughly washed.

The activated resin was subsequently converted to Fmoc-AzaGly-Rink by addition of Fmoc-hydrazide (1 g, 3 eq.) in DMF in the presence of DIEA (72 hours). The remaining amino acids were added with N-α-Fmoc protection following the procedure previously described in the general synthesis of the invention peptides.

The peptide was then cleaved from the resin and 0.265 g (50% yield) of crude product was obtained. The peptide was purified in two steps by reverse phase chromatography, the first step using a linear gradient of from 10 to 80% of eluent B over 30 min., and the second step using a linear gradient of from 20 to 60% of eluent B over 30 min.

After the second purification step the fractions with a purity >98% were pooled and lyophilized. 44 mg (17% yield) of purified peptide were obtained.

Mass spectral analysis—ES+ mode:
expected value: 1249.5 (average)
found: 1248.6 (monoisotopical).
net peptide content 80.5%; purity 98.2%; retention time 10.46 min.

EXAMPLE 15

(SEQ ID NO: 27): pGlu-His-Trp-Ser-Tyr-SPL-Hol-Arg-Pro-NEt

Fmoc-SPL-Hol-OH was synthesised according to Hinds et al. (8) and Ward et al. (9). The intermediate dipeptide was controlled by mass spectral analysis.

The value obtained was consistent with theory.

The synthesis and cleavage of the peptide were performed using the strategy described for example 9.

Purification was carried out using a linear gradient of from 20 to 80% of eluent B over 30 min.

26 mg (approximate yield 10%) of purified material were obtained.

Mass spectral analysis—FAB+ mode:
expected: 1233.5
found: 1233.4 (MH+)
net peptide content 73.9%; purity 97.5%; retention time 8.77 min.

EXAMPLE 16

(SEQ ID NO: 11): pGlu-His-Trp-Ser-Tyr-SPL-Npg-Arg-Pro-NEt

Fmoc-SPL-Npg-OH was synthesised according to Hinds et al. (8) and Ward et al. (9). The intermediate dipeptide was controlled by mass spectral analysis.

The value obtained was consistent with theory.

The synthesis and cleavage of the peptide were performed using the strategy described for example 9.

Purification was carried out using a linear gradient of from 30 to 70% of eluent B over 30 min.

53 mg (approximate yield 15%) of purified material were obtained.

Mass spectral analysis—ES+ mode:
expected: 1233.5
found: 1233.1 (average)
net peptide content 72.1%; purity 98.1%; retention time 8.52 min.

EXAMPLE 17

(SEQ ID NO: 12): pGlu-His-Trp-Ser-Tyr-SPL-Tle-Arg-Pro-NEt

Fmoc-SPL-Tle-OH was synthesised according to Hinds et al. (8) and Ward et al. (9). The intermediate dipeptide was controlled by mass spectral analysis.

The value obtained was consistent with theory.

The synthesis and cleavage of the peptide were performed using the strategy described for Example 9.

The peptide was purified in two steps, the first step using a linear gradient of from 20 to 60% of eluent B over 30 min., and the second step using a linear gradient of from 25 to 65% of eluent B over 30 min.

6 mg (approximate yield 3%) of purified material were obtained.

Mass spectral analysis—ES+ mode:
expected value: 1218.6
found: 1219.2 (average)
net peptide content 71.3%; purity: 97.8%; retention time 13.44 min.

EXAMPLE 18

(SEQ ID NO: 29): pGlu-His-Trp-Ser-Tyr-SPL-Nle-Arg-Pro-NEt

Fmoc-SPL-Nle-OH was synthesised according to Hinds et al. (8) and Ward et al. (9). The intermediate dipeptide was controlled by mass spectral analysis.

The value obtained was consistent with theory.

The synthesis and cleavage of the peptide were performed using the strategy described for example 9.

Purification was carried out using a linear gradient of from 20 to 80% of eluent B over 30 min.

44 mg (approximate yield 20%) of purified material were obtained.

Mass spectral analysis—ES+ mode:
expected: 1218.6
found: 1218.9 (average)
net peptide content 69.4%; purity 98.3%; retention time 13.91 min.

EXAMPLE 19

(SEQ ID NO: 13): pGlu-His-Trp-Ser-Tyr-SPL-Cha-Arg-Pro-NEt

Fmoc-SPL-Cha-OH was synthesised according to Hinds et al. (8) and Ward et al. (9). The intermediate dipeptide was controlled by mass spectral analysis.

The value obtained was consistent with theory.

The synthesis and cleavage of the peptide were performed using the strategy described for example 9.

Purification was carried out using a linear gradient of from 25 to 80% of eluent B over 30 min.

16 mg (approximate yield 14%) of purified material were obtained.

Mass spectral analysis—ES+ mode: expected: 1258.4
found: 1259.1 (average)
net peptide content 72.3%; purity 96%; retention time 14.20 min.

EXAMPLE 20

(SEQ ID NO: 29): pGlu-DPhe-Trp-Ser-Tyr-SPL-Leu-Arg-Pro-Gly-NH$_2$

The synthesis was carried out on 4-methylbenzhydrylamine resin.

D-alanine, proline and arginine were introduced using a t-Boc strategy as described above for the general synthesis of the invention peptides.

The synthesis was started with Boc-Gly-OH. The subsequent amino acids were incorporated via a Fmoc strategy as described above.

The peptides were deprotected and cleaved from the resin using HF as described above.

Purification was carried out using a linear gradient of from 30 to 80% of eluent B over 30 min.

25 mg (approximate yield 5%) of purified material were obtained.

Mass spectral analysis—ES+ mode:
expected: 1257.5
found: 1258.3 (average)
net peptide content 78.5%; purity 97.3%; retention time 17.44 min.

EXAMPLE 21

(SEQ ID NO: 30): pGlu-DPhe-Trp-Ser-Tyr-SPL-Leu-Arg-Pro-DAlaNH$_2$

Synthesis and cleavage were carried out as described for example 20.

Purification was carried out using a linear gradient of from 25 to 80% of eluent B over 30 min.

27 mg (approximate yield 6%) of purified material were obtained.

Mass spectral analysis—ES+ mode
expected: 1272.5
found: 1272.6 (average)
net peptide content 78.3%; purity 99%; retention time 18.03 min.

EXAMPLE 22
(SEQ ID NO: 14): AcDNal-DpClPhe-DTrp-Ser-Tyr-SPL-Leu-Arg-Prx)-DAlaNH$_2$

Synthesis and cleavage were carried out as described for example 20.

The peptide was purified in two steps, the first step using a linear gradient of from 30 to 100% of eluent B over 30 min., and the second step using a linear gradient of from 35 to 70% of eluent B over 30 min.

6 mg (approximate yield 2%) of purified material were obtained.
Mass spectral analysis—ES+ mode:
expected value: 1435.1
found: 1434.7 (average)
net peptide content 78.0%; purity: 98%; retention time 16.92 min.

EXAMPLE 23
(SEQ ID NO: 15): AcDNal-DpClPhe-DPal-Ser-Tyr-SPL-Leu-Arg-Pro-DAlaNH$_2$

Synthesis and cleavage were carried out as described for example 20.

Purification was carried out using a linear gradient of from 25 to 80% of eluent B over 30 min.

21 mg (approximate yield 5%) of purified material were obtained.
Mass spectral analysis—ES+ mode:
expected: 1397.1
found: 1396.8 (average)
net peptide content 70.9%; purity 98.8%; retention time 17.91 min.

EXAMPLE 24
(SEQ ID NO: 16): AcDNal-DpClPhe-DBal-Ser-Tyr-SPL-Leu-Arg-Pr-DAlaNH$_2$

Synthesis and cleavage were carried out as described for example 20.

Purification was carried out using a linear gradient of from 30 to 100% of eluent B over 30 min.

13 mg (approximate yield 3%) of purified material were obtained.
Mass spectral analysis—ES+ mode:
expected: 1452.1
found: 1451.6 (average)
net peptide content 82.4%; purity 96.4%; retention time 18.52 min.

EXAMPLE 25
(SEQ ID NO: 31): AcDNal-DpClPhe-DPal-Ser-Tyr-SPL-Npg-Arg-Pro-DAlaNH$_2$

Synthesis and cleavage were carried out as described for example 20.

Purification was carried out using a linear gradient of from 20 to 60% of eluent B over 30 min.

10 mg (4% yield) of purified material were obtained.
Mass spectral analysis—ES+ mode:
expected value: 1410.6
found: 1410.7
net peptide content 74.8%; purity 93.1%; retention time 13.38 min.

EXAMPLE 26
(SEQ ID NO: 32): AcDNal-DpClPhe-DPal-Ser-NicLys-SPL-Npg-Arg-Pro-DAlaNH$_2$

Synthesis and cleavage were carried out as described for example 20.

Purification was carried out using a linear gradient of from 20 to 60% of eluent B over 30 min.

73 mg (20% yield) of purified material were obtained.
Mass spectral analysis—ES+ mode:
expected value: 1481.0
found: 1481.0
net peptide content 79%; purity: 99%; retention time 17.82 min.

EXAMPLE 27
(SEQ ID NO: 17): AcDNal-DpCtPhe-DPal-Ser-IprLys-SPL-Npg-Arg-Pro-DAlaNH$_2$

Synthesis and cleavage were carried out as described for example 20.

Purification was carried out using a linear gradient of from 15 to 50% of eluent B over 30 min.

78 mg (approximative yield 30%) of purified material were obtained.
Mass spectral analysis—ES+ mode:
expected value: 1417.8
found: 1418.4
net peptide content 71.2%; purity: 98.8%; retention time 16.04 min.

EXAMPLE 28
(SEQ ID NO: 33): AcDNal-DpCtPhe-DPal-Ser-Tyr-SPL-Npg-IprLys-Pro-DAlaNH$_2$

Synthesis and cleavage were carried out as described for example 20.

Purification was carried out using a linear gradient of from 20 to 60% of eluent B over 30 min.

85 mg (approximative yield 20%) of purified material were obtained.
Mass spectral analysis—ES+ mode
expected value: 1424.9
found: 1425.1
net peptide content 72.7%; purity: 97.5%; retention time 19.39 min.

EXAMPLE 29
(SEQ ID NO: 34): AcDNal-DpClPhe-DPal-Ser-NicLys-SPL-Npg-IprLys-Pro-DAlaNH$_2$

Synthesis and cleavage were carried out as described for example 20.

Purification was carried out using a linear gradient of from 15 to 65% of eluent B over 30 min.

97 mg (33% yield) of purified material were obtained.
Mass spectral analysis—ES+ mode:
expected value: 1495.1
found: 1495.7
net peptide content 70.5%; purity: 97.5%; retention time 18.66 min.

REFERENCES
(1) G. BARANY and R. B. MERRIFIELD (1979) The Peptides, Analysis, Synthesis, Biology, Vol. 2, Chapter 1.
(2) E. ATHERTON and R. C. SHEPPARD (1989) Solid phase peptide synthesis, IRL Press, OXFORD
(3) D. Le NGUEN, A. HEITZ and B. CASTRO (1987) J. Chem. Soc. Perkin Trans. I, 1915

(4) E. KAISER, R. L. COLESCOTT, C. D. BOSSINGER and P. I. COOK (1970) Anal. Biochem., 34, 595
(5) M. BODANSZKY and A. BODANSZKY (1994) The practice of peptide synthesis, Springer Verlag Berlin
(6) P. N. RAO, J. E. BURDETT Jr, J. W. CESSAD, C. M. DI NUNNO, D. M. PETERSON and H. K. KIM (1987) Int. J. Pept. Protein Res., 29, 118
(7) J. R. Mc DERMOTT and N. L. BENOITON (1973) Can. J. Chem. L, 1915
(8) M. G. HINDS, N. G. J. RICHARDS and J. A. ROBINSON (1988) J. Chem. Soc. Chem. Commun, 1447
(9) P. WARD, G. B. EWAN, C.C. JORDAN, S. J. IRELAND, R. M. HAGAN and J. R. BROWN (1990) J. Med. Chem., 33, 1848.

We claim:

1. A peptide of the formula (SEQ ID N° 1):

$$A_1-A_2-W-A_3-A_4-SPL-A_5-AG-Pro-Z \quad (I)$$

in which:

- $A_1$ is pGlu, AcSar or an aromatic D-amino acid;
- $A_2$ is a direct bond, His, DPhe, DpFPhe or DpClPhe;
- *W is an aromatic L- or D-amino acid;
- $A_3$ is Ala, Thr, Ser, DSer, Ser(OBzl) or MeSer;
- $A_4$ is Tyr, Phe, cPzACAla, L- or D-PicLys, L- or D-NicLys or L- or D-IprLys;

*SPL is the spirolactam of formula

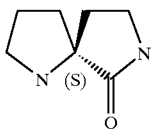

[* Y is the dipeptide $A_5A_6$ in which]

-$A_5$ is an amino acid with a ($C_1$–$C_8$)alkyl or ($C_3$–$C_6$) cycloalkyl side chain;

-$A_6$ is L- or D-(Arg, HArg, Lys, HLys, Orn, Cit, HCit or Aph), where L- or D-(Arg and HArg) can be substituted by one or two ($C_1$–$C_4$)alkyl groups and L- or D-(Lys, HLys, Orn and Aph) can be substituted by an isopropyl, nicotinoyl or picolinoyl group; and

*Z is $GlyNH_2$, $DAlaNH_2$, $AzaGlyNH_2$ or —$NHR_1$ where $R_1$ is a ($C_1$–$C_4$)alkyl optionally substituted by a hydroxy or one or several fluorine atoms, a ($C_3$–$C_6$) cycloalkyl or a heterocyclic radical selected from the group consisting of morpholinyl, pyrrolidinyl and piperidyl;

or its pharmaceutically acceptable salts.

2. A peptide according to claim 1,
in which:
-$A_1$ is pGlu or AcSar;
-$A_2$ is His
*W is a L-amino acid;
-$A_4$ is Tyr or Phe;
-$A_6$ is Arg, Lys, HArg, HLys, Orn, Cit or HCit; and
*Z is $GlyNH_2$, $AzaGlyNH_2$ or —$NHR_1$;
or pharmaceutically acceptable salts.

3. A peptide according to claim 2,
in which:
*$A_4$ is Tyr;
*$A_6$ is Arg; and
*Z is $GlyNH_2$;
or its pharmaceutically acceptable salts.

4. A peptide according to claim 3, in which $A_1$ is pGlu and $A_3$ is Ser, or its pharmaceutically acceptable salts.

5. A peptide according to claim 3, in which $A_1$ is pGlu and W is Trp, or its pharmaceutically acceptable salts.

6. A peptide according to claim 2,
in which:
*$A_3$ is Ser;
*$A_4$ is Tyr;
*$A_6$ is Arg; and
*Z is —$NHR_1$ with $R_1$ being ethyl;
or its pharmaceutically acceptable salts.

7. A peptide according to claim 2,
in which:
*$A_3$ is Ser;
*$A_4$ is Tyr;
*$A_6$ is Arg; and
*Z is $AzaGlyNH_2$;
or its pharmaceutically acceptable salts.

8. A peptide according to claim 1,
in which
-$A_1$ is pGlu or an aromatic D-amino acid;
-$A_2$ is a direct bond, DPhe, DpFPhe or DpClPhe;
*W is Trp, DTrp, DPhe, DpClPhe, DNal, DPal or DBal;

-$A_3$ is Ser;
-$A_4$ is Tyr, Phe, cPzACAla, L- or D-PicLys, L- or D-NicLys or L- or D-IprLys; and
*Z is $GlyNH_2$ or $DAlaNH_2$;
or its pharmaceutically acceptable salts.

9. A peptide according to claim 8,
in which:
*$A_4$ is Tyr; and
*$A_6$ is Arg;
or its pharmaceutically acceptable salts.

10. A peptide according to claim 8, in which $A_1$ is AcDNal, $A_2$ is DpClPhe, $A_5$ is Npg and Z is $DAlaNH_2$,
or its pharmaceutically acceptable salts.

11. A peptide according to claim 9, in which $A_1$ is AcDNal, $A_2$ is DpClPhe and Z is $DAlaNH_2$,
or its pharmaceutically acceptable salts.

12. A pharmaceutical composition which comprises a therapeutically effective amount of a peptide according to claim 1 or a pharmaceutically acceptable salt thereof.

13. A pharmaceutical composition according to claim 12 for parenteral administration.

14. A pharmaceutical composition which comprises a therapeutically effective amount of a peptide according to claim 2 or a pharmaceutically acceptable salt thereof.

15. A pharmaceutical composition which comprises a therapeutically effective amount of a peptide according to claim 3 or a pharmaceutically acceptable salt thereof.

16. A pharmaceutical composition which comprises a therapeutically effective amount of a peptide according to claim 4 or a pharmaceutically acceptable salt thereof.

17. A pharmaceutical composition which comprises a therapeutically effective amount of a peptide according to claim 5 or a pharmaceutically acceptable salt thereof.

18. A pharmaceutical composition which comprises a therapeutically effective amount of a peptide according to claim 6 or a pharmaceutically acceptable salt thereof.

19. A pharmaceutical composition which comprises a therapeutically effective amount of a peptide according to claim 7 or a pharmaceutically acceptable salt thereof.

20. A pharmaceutical composition which comprises a therapeutically effective amount of a peptide according to claim 8 or a pharmaceutically acceptable salt thereof.

21. A pharmaceutical composition which comprises a therapeutically effective amount of a peptide according to claim 9 or a pharmaceutically acceptable salt thereof.

22. A pharmaceutical composition which comprises a therapeutically effective amount of a peptide according to claim 10 or a pharmaceutically acceptable salt thereof.

23. A pharmaceutical composition which comprises a therapeutically effective amount of a peptide according to claim 11 or a pharmaceutically acceptable salt thereof.

24. A method of treating infertility or hypegonadic or hypergonadic states, which comprising administering to a subject in need thereof a therapeutically effective amount of a peptide according to claim 1 or a pharmaceutically acceptable salt thereof.

25. A method according to claim 24 wherein said peptide is administered in combination with a therapeutically effective amount of a sex steroid or a gonadotrophin.

26. A contraceptive method, which comprises administering to a subject in need thereof a therapeutically effective amount of a peptide according to claim 1 or a pharmaceutically acceptable salt thereof.

27. A method according to claim 26, wherein said peptide is administered in combination with a therapeutically effective amount of a sex steroid or a gonadotrophin.

28. A method of treating or preventing prostate cancer or benign prostatic hypertrophy, which comprises administering to a subject in need thereof a therapeutically effective amount of a peptide according to claim 1 or a pharmaceutically acceptable salt thereof.

29. A method according to claim 28, wherein said peptide is administered in combination with a therapeutically effective amount of an androgen action inhibitor, a 5α-reductase inhibit or $C_{17-20}$ lyase inhibitor.

30. A method of treating or preventing breast cancer, which comprises administering to a subject in need thereof a therapeutically effective amount of a peptide according to claim 1 or a pharmaceutically acceptable salt thereof.

31. A method according to claim 30, wherein said peptide is administered in combination with a therapeutically effective amount of an antiestrogen, an aromatase inhibitor or a $C_{17-20}$ lyase inhibitor.

32. A method of treating or preventing sex hormone-related benign or malignant tumors, which comprises administering to a subject in need thereof a therapeutically effective amount of a peptide according to claim 1 or a pharmaceutically acceptable salt thereof.

33. A method according to claim 32, wherein said peptide is administered in combination with a therapeutically effective amount of a hormonal or antitumoral agent.

34. A method of treating or preventing sex hormone-independent but LH-RH sensitive benign or malignant tumors, which comprises administering to a subject in need thereof a therapeutically effective amount of a peptide according to claim 1 or a pharmaceutically acceptable salt thereof.

35. A method according to claim 34, wherein said peptide is administered in combination with a therapeutically effective amount of an antitumoral agent.

36. A method of treating or preventing benign or malignant lymphoproliferative disorders, which comprises administering to a subject in need thereof a therapeutically effective amount of peptide according to claim 1 or a pharmaceutically acceptable salt thereof.

37. A method according to claim 36, wherein said peptide is administered in combination with a therapeutically effective amount of an immunomodulating agent or an immunosuppressive agent.

* * * * *